United States Patent
Klubben, III et al.

(10) Patent No.: US 10,154,779 B2
(45) Date of Patent: Dec. 18, 2018

(54) CONTROLLED VARIABLE LENGTH AND ILLUMINATION PATTERN LIGHT DIFFUSING OPTICAL FIBER

(71) Applicant: Corning Incorporated, Corning, NY (US)

(72) Inventors: William Spencer Klubben, III, Corning, NY (US); Jeffrey L Mooney, Fayetteville, PA (US); Peter Gerard Wigley, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 202 days.

(21) Appl. No.: 15/072,879

(22) Filed: Mar. 17, 2016

(65) Prior Publication Data

US 2016/0278622 A1    Sep. 29, 2016

Related U.S. Application Data

(60) Provisional application No. 62/137,869, filed on Mar. 25, 2015.

(51) Int. Cl.
*A61B 1/07*    (2006.01)
*G02B 23/24*    (2006.01)
(Continued)

(52) U.S. Cl.
CPC .............. *A61B 1/07* (2013.01); *A61N 5/0601* (2013.01); *A61N 5/062* (2013.01); *G02B 6/001* (2013.01); *G02B 6/3624* (2013.01); *G02B 23/2469* (2013.01); *A61N 2005/063* (2013.01); *G02B 5/02* (2013.01); *G02B 6/0003* (2013.01); *G02B 6/0051* (2013.01); *G02B 6/02347* (2013.01)

(58) Field of Classification Search
CPC combination set(s) only.
See application file for complete search history.

(56) References Cited

U.S. PATENT DOCUMENTS 5,074,632 A    12/1991    Potter
5,303,324 A    4/1994    Lundahl
(Continued)

FOREIGN PATENT DOCUMENTS

CA    2028757 C    4/1998
WO    2010011299    1/2010
WO    2012162503    4/2014

OTHER PUBLICATIONS

International Search Report and Written Opinion PCT/US2016/023376 dated May 30, 2016.

*Primary Examiner* — Scott T Luan
(74) *Attorney, Agent, or Firm* — Payal A. Patel

(57) ABSTRACT

An illuming device for use in medically illuminating tissue of interest within a patient generally includes a light diffusing optical fiber and an at least partially optically opaque sheath that is mounted over the fiber for selective, sliding movement along the length thereof. By sliding the sheath relative to the optical fiber after it has been inserted into a patient to illuminate a particular area of tissue, the length, size, and/or shape of the light that is exposed to the tissue can be selectively controlled. Such in situ variation of the properties of the exposed light permit use of a single instrument and a single procedure regardless of variation in the size and shape of the diseased tissue being medically treated.

18 Claims, 2 Drawing Sheets

(51) Int. Cl.
  *F21V 8/00* (2006.01)
  *A61N 5/06* (2006.01)
  *G02B 6/36* (2006.01)
  *G02B 5/02* (2006.01)
  *G02B 6/02* (2006.01)

(56) References Cited

U.S. PATENT DOCUMENTS

| | | |
|---|---|---|
| 5,431,647 A | 7/1995 | Purcell, Jr. |
| 8,492,448 B2 | 7/2013 | Dewa |
| 8,591,087 B2 | 11/2013 | Bickham |
| 8,620,125 B2 | 12/2013 | Button |
| 8,787,717 B2 | 7/2014 | Logunov |
| 8,805,141 B2 | 8/2014 | Fewkes |
| 8,897,611 B2 | 11/2014 | Genier |
| 8,926,143 B2 | 1/2015 | Le et al. |
| 8,929,703 B2 | 1/2015 | Logunov |
| 8,953,914 B2 | 2/2015 | Genier |
| 9,025,923 B2 | 5/2015 | Logunov |
| 9,093,003 B2 | 7/2015 | Logunov |
| 9,217,826 B2 | 12/2015 | Logunov |
| 2001/0037080 A1 | 11/2001 | Mueller et al. |
| 2007/0239232 A1 | 10/2007 | Kurtz et al. |
| 2008/0194973 A1* | 8/2008 | Imam ............ A61B 19/54 600/478 |
| 2013/0107565 A1 | 5/2013 | Genier |
| 2013/0308335 A1 | 11/2013 | Genier |
| 2014/0276691 A1* | 9/2014 | Iwamasa ......... G02B 6/262 606/12 |
| 2014/0301699 A1 | 10/2014 | Goldfab et al. |

\* cited by examiner

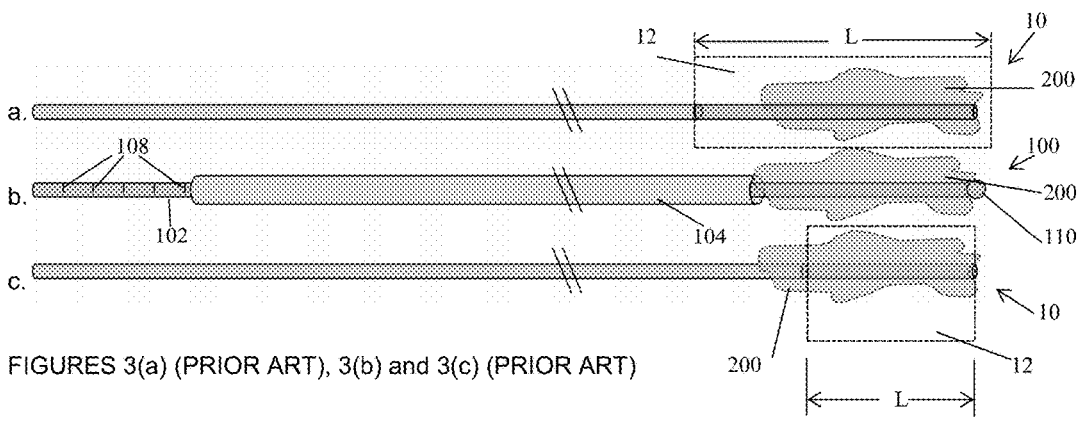
FIGURES 3(a) (PRIOR ART), 3(b) and 3(c) (PRIOR ART)

CONTROLLED VARIABLE LENGTH AND ILLUMINATION PATTERN LIGHT DIFFUSING OPTICAL FIBER

This application claims the benefit of priority under 35 U.S.C. § 119 of U.S. Provisional Application Ser. No. 62/137,869 filed on Mar. 25, 2015 the content of which is relied upon and incorporated herein by reference in its entirety.

BACKGROUND

1. Field of Invention

The present invention relates generally to optical fiber, and more particularly to optical fiber used to transmit light for medical treatments.

2. Background of Art

Photodynamic therapy (PDT) is a treatment that uses a drug, called a photosensitizer or photosensitizing agent, and a particular type of light. When photosensitizers are exposed to a specific wavelength of light, they produce a form of oxygen that kills nearby cells.

Each photosensitizer is activated by light of a specific wavelength. This wavelength determines how far the light can travel into the body. Thus, doctors use specific photosensitizers and wavelengths of light to treat different areas of the body with PDT.

In the first step of PDT for cancer treatment, a photosensitizing agent is injected into the bloodstream. The agent is absorbed by cells all over the body but stays in cancer cells longer than it does in normal cells. Approximately 24 to 72 hours after injection, when most of the agent has left normal cells but remains in cancer cells, the tumor is exposed to light. The photosensitizer in the tumor absorbs the light and produces an active form of oxygen that destroys nearby cancer cells.

In addition to directly killing cancer cells, PDT appears to shrink or destroy tumors in two other ways. The photosensitizer can damage blood vessels in the tumor, thereby preventing the cancer from receiving necessary nutrients. PDT also may activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer.

PDT is usually performed as an outpatient procedure. PDT may also be repeated and may be used with other therapies, such as surgery, radiation, or chemotherapy.

Commonly in use in PDT are plastic cylindrical diffusers used to illuminate the cancer cells. With specific reference to FIG. 1, these cylindrical diffusers 10 are available only in fixed lengths L and illuminate uniformly throughout the entire length of the diffuser; light is not diffused from the area of the diffuser outside dotted box 12. Because tissue to be illuminated in medical procedures, such as, for example, cancerous tumors, are generally not regular or uniform, there is a need to specifically alter the illumination pattern of a cylindrical diffuser. Additionally, regardless of preoperative planning techniques, there is not a method for adjusting the amount of illumination in situ without replacing the diffuser.

Corning Incorporated offers a technology sold under the brand name FIBRANCE® light diffusing fiber in the medical space. U.S. Patents directed to this diffusing fiber include U.S. Pat. No. 8,591,087 and U.S. Pat. No. 8,926,143, the disclosures of which are hereby incorporated by reference in their entirety herein.

As stated, current technology requires discrete length diffusion fibers to be used; if a different sized diffuser is needed a new device must be opened and inserted into the patient. Such a process wastes time and increases expense associated with the procedure.

3. Illustrative Objects and Advantages

It is therefore an object and advantage of the present invention to provide a use for a single diffusing fiber and an opaque sheath or patterned sheath to control exposure of the fiber to the surrounding tissue.

It is another object and advantage of the present invention to provide use of a diffusing fiber that decreases costs associated with certain medical procedures, decreases time associated with certain medical procedures, and decreases damage to surrounding healthy tissue during certain medical procedures.

Other objects and advantages of the present invention will in part be obvious and in part appear hereinafter.

SUMMARY OF THE INVENTION

In accordance with the foregoing illustrative objects and advantages, the present invention provides a light diffusing optical fiber and an at least partially optically opaque sheath that is mounted over the fiber for selective, sliding movement along the length thereof. By sliding the sheath relative to the optical fiber after it has been inserted into a patient to illuminate a particular area of tissue, the length, size, and/or shape of the light that is exposed to the tissue can be selectively controlled. Such in situ variation of the properties of the exposed light permit use of a single instrument and a single procedure regardless of variation in the size and shape of the diseased tissue being medically treated.

In one aspect, the invention provides a method for using a light diffusing optical fiber to treat tissue in a patient, including the steps of: stabilizing an illumination catheter in a position suitable to illuminate the tissue; sliding a first sheath through the illumination catheter, wherein the first sheath is at least partially visually opaque; sliding a light diffusing fiber through the first sheath; moving the first sheath along the length of the light diffusing fiber such that a portion of the light diffusing fiber is able to illuminate the tissue; and providing light to the light diffusing fiber, the light passing through the portion of the light diffusing fiber and illuminating the tissue.

In an embodiment, the method further includes sliding the first sheath to vary the length of the portion of the light diffusing fiber able to illuminate the tissue.

In an embodiment, the first sheath includes opaque regions and transparent regions, and the method further includes: determining the shape of the tissue, and configuring the opaque regions of the first sheath in a pattern that is the inverse of the shape of the tissue, so that the transparent regions of the first sheath have a configuration that corresponds with the shape of the tissue.

In an embodiment, the method further includes stabilizing the first sheath while in situ. In this embodiment, the method further includes the step of sliding a second sheath over the first sheath, wherein the second sheath is visually opaque.

In an embodiment, the step of moving the first sheath includes moving the first sheath along the length of the light diffusing fiber such that the length of light diffusing fiber exposed to the diseased tissue is substantially the same as the length of the tissue.

In another aspect, the invention provides an illuminating device, including: an elongated light diffusing optical fiber having proximal and distal ends; and an opaque sheath having proximal and distal ends and positioned in partially covering relation to the light diffusing optical fiber for reciprocating sliding movement along the length thereof.

In an embodiment, the elongated light diffusing optical fiber further includes a plurality of distance markings visibly displayed thereon and extending in predetermined, spaced intervals from the fiber's proximal end over a predetermined portion of the length thereof. In a further embodiment, the opaque sheath is of a predetermined length that relates to the plurality of distance markings displayed on the elongated light diffusing optical fiber in that alignment of the proximal end of the opaque sheath with any of the plurality of distance markings corresponds with the distal end of the opaque sheath being spaced from the distal end of the light diffusing optical fiber by a known distance, thereby permitting visual confirmation of the length of an uncovered portion of the light diffusing fiber.

In an embodiment, the opaque sheath is radio opaque.

In another aspect, the invention provides a device for illuminating tissue, including: an elongated light diffusing optical fiber of predetermined length and having proximal and distal ends; and a partially transparent sheath of a predetermined length shorter than the predetermined length of the elongated light diffusing optical fiber and having a visually opaque coating applied to a portion thereof in a pattern that is the inverse of the shape of the tissue, thereby leaving a transparent area that has the same shape as the shape of the tissue, wherein the partially transparent sheath is positioned in partially covering relation to the light diffusing optical fiber for reciprocating sliding movement along the length thereof.

In an embodiment, the device further includes a visually opaque sheath having proximal and distal ends, the visually opaque sheath positioned in covering relation to the partially transparent sheath for reciprocating sliding movement along the length thereof, whereby the visually opaque sheath permits additional control in situ over the light emitted from the light diffusing optical fiber. In a further embodiment, the visually opaque sheath and the partially transparent sheath are both radio opaque. In a further embodiment, the device further includes a stabilization mechanism coupled to the partially transparent sheath for purposes of permitting in situ stabilization thereof.

In an embodiment, the opaque sheath includes an interior surface that is metallic.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings are illustrative of selected aspects of the present disclosure, and together with the description serve to explain principles and operation of methods, products, and compositions embraced by the present disclosure.

BRIEF DESCRIPTION OF THE DRAWINGS

The present invention will be more fully understood and appreciated by reading the following Detailed Description in conjunction with the accompanying drawings, in which:

FIG. 3a is an elevation view of a prior art light diffusing fiber and fixed sheath shown overexposing diseased tissue.

FIG. 3b is an elevation view of a light diffusing fiber and movable sheath shown relative to diseased tissue.

FIG. 3c is an elevation view of a light diffusing fiber and fixed sheath underexposing diseased tissue.

DETAILED DESCRIPTION

Figures 2A, 2B:
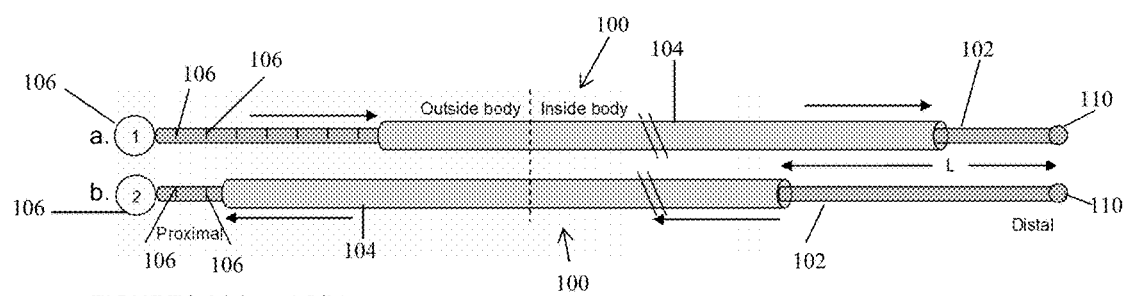
FIGS. 2a and 2b are elevation views of a light diffusing fiber with a movable sheath shown in two positions relative to the fiber.

Referring now to the drawings, in which like reference numerals refer to like parts throughout, there is seen in FIGS. 2(a) and 2(b) an illuminating device 100 generally comprising a light diffusing fiber 102 and a sheath 104 positioned in partially covering relation to light diffusing optical fiber 102 for reciprocating sliding movement along the length thereof. A light source, shown schematically by reference numeral 106, generates and distributes light energy to diffusing fiber 102 for purposes of illuminating tissue within a patient for medical purposes. For non-limiting examples, illuminating device 100 may be used to illuminate diseased tissue using PDT or it may be used to illuminate healthy tissue for purposes of performing a fluorescent study or as part of a diagnostic diffuse spectroscopy procedure.

In using illuminating device 100, a medical service provider would first gain access to an internal body region of interest through introduction of an illumination (e.g., transparent) catheter (not shown). Once the catheter is stabilized within the patient, the medical service provider would pass illumination device 100 there through until the distal end of light diffusing fiber 102 extends outwardly beyond the end of sheath 104. Sheath 104 may then be slid distally or proximally along the length of light diffusing fiber 102 exposing the desired length thereof for purposes of performing the medical procedure. In one embodiment, the proximal end of light diffusing fiber 102 includes distance markings 108 printed thereon such that the medical provider can gauge and selectively alter, in situ, the length of diffusing fiber 102 left exposed by the sheath 104. In addition, sheath 104 and the distal end 110 of light diffusing fiber 102 are both radio-opaque and visibly opaque for purposes of permitting the medical provider to view the position of thereof via fluoroscopy, in situ. Thus, distance markings 108 and the radio-opaque/visibly opaque nature of distal end 110 and sheath 104 permit precise positioning of illuminating device 100, in situ.

Figure 1:
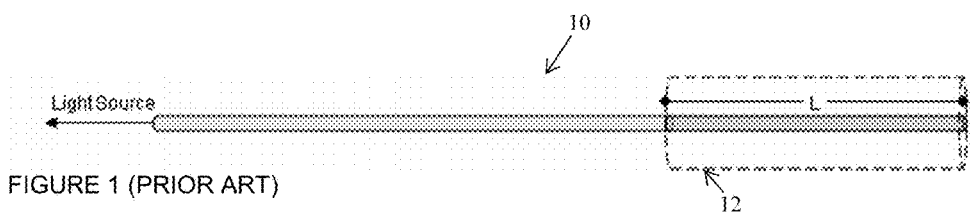
FIG. 1 is an elevation view of a prior art light diffusing fiber having a fixed sheath.

Referring to FIGS. 3(a)-3(c), illustrative examples of the benefits of the device of FIG. 2 over the Prior Art device of FIG. 1 are shown. A non-uniformly shaped area of tissue 200 to be illuminated is shown in FIGS. 3(a)-3(c); this tissue 200 may, for example, represent a cancerous tumor. In the example provided in FIGS. 3(a) and 3(c), a prior art illumination device 10 having a light diffusing length L diffuses light in the area generally represented by box 12. In FIG. 3(a), because tissue 200 is of a size and shape not the same as length L, but indeed of a substantially shorter length, diffusing fiber 10 is illuminating a substantial amount of tissue surrounding the tissue of interest 200, thereby overexposing the patient to the light energy. Similarly in FIG. 3(c), the length L of light diffusing fiber 10 is of a length that is substantially shorter than the length and shape of tissue 200, thereby under-exposing the tissue of interest to light energy. In the example of FIG. 3(c), a second procedure would thus be needed to fully illuminate the tissue of interest using a second light diffusing fiber of diffusing length sufficient to illuminate the area on unexposed tissue from the first procedure. In comparison, FIG. 3(b) reveals use of illuminating device 100, whereby sheath 104 is slidably positioned to permit exposure of the same length of light diffusing fiber 10 as the length of tissue 200, thereby not producing substantially more or less light energy than is necessary to accurately illuminate the tissue of interest.

Figure 4:
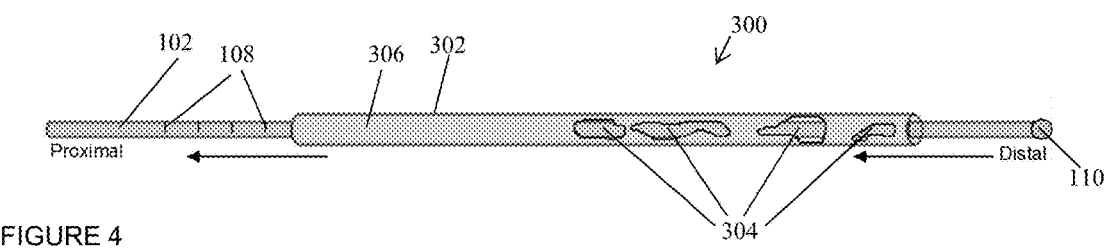
FIG. 4 is an elevation view of a light diffusing fiber and movable sheath that is partially transparent and partially opaque.

Referring to FIG. 4, an illuminating device 300 comprises a light diffusing fiber 102 (the same light diffusing fiber as provided with illuminating device 100), having distance markings 108 displayed on at least a portion of the proximal length thereof, and a visibly opaque and radio opaque distal end 110. A sheath 302 is positioned in slidable relation over light diffusing fiber 102, similar to the manner in which sheath 104 is positioned over light diffusing fiber 102 in illuminating device 100. Sheath 302, however, includes transparent areas 304, as well as visibly opaque (and radio opaque) areas 306. Thus, light energy diffused from fiber 102 will also be diffused through transparent areas 304 but will be blocked by visibly opaque areas 306. Such a patterned sheath 302 may be useful when needing to illuminate a uniquely shaped area of tissue. As an additional element of in situ control, an additional opaque sheath (not shown) may be slidably positioned over sheath 302. Using the additional opaque sheath provides the medical service provider the ability to control the illumination parameters more precisely.

In using illuminating device 300, a medical service provider may image an area of tissue to identify the shape and size of the tissue to be illuminated, using traditional imaging techniques (e.g., MRI, CT, etc.) to create a pre-surgical plan and define illumination requirements. The inverse of the shape and size of the imaged tissue of interest may then be mapped onto a transparent sheath such that areas not to have light energy diffused there through will be coated with an opaque coating, such as printed with an opaque ink. This could be done, for example, in a medical procedure room wherein a digital image of the tissue to be illuminated is saved in a format suitable for being read by a computer aided manufacturing machine, such as a 3-D printer, and sheath 302 can be manufactured (e.g., 3-D printed) in the procedure room for ready use.

Figure 5:
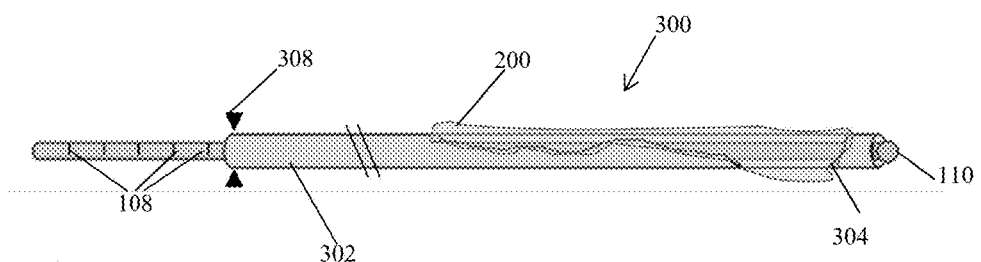
FIG. 5 is an elevation view of a light diffusing fiber and movable sheath that is partially transparent and partially opaque shown in relation to diseased tissue to be treated.

Referring to FIG. 5, the sheath 302 of illumination device 300 may be made with a transparent area 304 that fully corresponds in shape to the tissue 200 to be illuminated, thereby not requiring diffusion of light through unsheathed portions of light diffusing fiber 102. Such a sheath 302 maximizes illumination of the tissue desired to be illuminated while minimizing the illumination of tissue not intended to be illuminated. In addition, it is advantageous to include a device 308 to stabilize sheath 302 while it is being used to illuminate tissue 200.

It should be noted that light diffusing fiber 102 can include traditional light diffusing fibers as well as other types of conduits from which light energy may be emitted, such as, for example, a patterned polymer waveguide or simply a cylindrical patterned diffuser designed with optimum properties for illumination. In addition, sheaths 104, 302 can be composed of conventional polymeric material with internal surfaces that are composed of a material which reflects a majority of the incident light, such as metallic, and may be biocompatible with variations in diffusion properties and in circumference. In addition, sheaths 104, 302 may include phosphors so that they fluoresce. In addition, the optical edge of the sheaths 104, 32 may be straight or miscellaneous shaped with differing color temperatures at different positions there along. Furthermore, the visually opaque regions of sheaths 104, 302 may act as a spectral filter or a polarizer to (possibly acting as a fluorescence or birefringence detector).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. A method for using a light diffusing optical fiber to illuminate tissue in a patient, comprising:
    a) stabilizing an illumination catheter in a position suitable to illuminate the tissue;
    b) sliding a first sheath through the illumination catheter, wherein the first sheath is at least partially visually opaque, the first sheath including opaque regions and transparent regions;
    c) determining the shape of the tissue;
    d) configuring the opaque regions of the first sheath in a pattern that is the inverse of the shape of the tissue, so that the transparent regions of the first sheath have a configuration that corresponds with the shape of the tissue;
    e) sliding a light diffusing fiber through the first sheath;
    f) moving the first sheath along the length of the light diffusing fiber such that a portion of the light diffusing fiber is able to illuminate the tissue; and
    g) providing light to the light diffusing fiber, the light passing through the portion of the light diffusing fiber and illuminating the tissue.

2. The method according to claim 1, further comprising sliding the first sheath to vary the length of the portion of the light diffusing fiber able to illuminate the tissue.

3. The method according to claim 1, further comprising stabilizing the first sheath while in situ.

4. The method according to claim 3, following the stabilizing the first sheath, further comprising sliding a second sheath over the first sheath, wherein the second sheath is visually opaque.

5. The method according to claim 1, prior to stabilizing the illumination catheter, comprising the further steps of providing a visually opaque sheath.

6. An illuminating device, comprising:
   a) an elongated light diffusing optical fiber having proximal and distal ends; and
   b) an at least partially opaque sheath having proximal and distal ends and positioned in partially covering relation to the light diffusing optical fiber for reciprocating sliding movement along the length thereof, the at least partially opaque sheath including opaque regions and transparent regions, the opaque regions configured in a pattern that is an inverse of a shape of a tissue and the transparent regions having a configuration corresponding to the shape of the tissue.

7. The device according to claim 6, wherein the elongated light diffusing optical fiber further comprises a plurality of distance markings visibly displayed thereon and extending in predetermined, spaced intervals from the proximal end over a predetermined portion of the length thereof.

8. The device according to claim 7, wherein the at least partially opaque sheath is of a predetermined length that relates to the plurality of distance markings displayed on the elongated light diffusing optical fiber in that alignment of the proximal end of the opaque sheath with any of the plurality of distance markings corresponds with the distal end of the opaque sheath being spaced from the distal end of the light diffusing optical fiber by a known distance, thereby permitting determination of the length of an uncovered portion of the light diffusing fiber.

9. The device according to claim 6, wherein the at least partially opaque sheath is radio opaque.

10. The device according to claim 6, wherein the elongated light diffusing optical fiber is illuminated and the at least partially opaque sheath comprises an interior surface that is composed of a material which reflects a majority of the illuminating light.

11. A device for illuminating tissue, comprising:
    a) an elongated light diffusing optical fiber of predetermined length and having proximal and distal ends; and
    b) a partially transparent sheath of a predetermined length shorter than the predetermined length of the elongated light diffusing optical fiber and having a visually opaque coating applied to a portion thereof in a pattern that is the inverse of the shape of the tissue, thereby leaving a transparent area that has the same shape as the shape of the tissue, wherein the partially transparent sheath is positioned in partially covering relation to the light diffusing optical fiber for reciprocating sliding movement along the length thereof.

12. The device according to claim 11, further comprising a visually opaque sheath having proximal and distal ends, the visually opaque sheath positioned in covering relation to the partially transparent sheath for reciprocating sliding movement along the length thereof.

13. The device according to claim 12, wherein the visually opaque sheath and the partially transparent sheath are both radio opaque.

14. The device according to claim 11, wherein the elongated light diffusing optical fiber further comprises a plurality of distance markings visibly displayed thereon and extending in predetermined, spaced intervals from the proximal end thereof over a predetermined portion of the length thereof.

15. The device according to claim 14, further comprising a visually opaque sheath having proximal and distal ends, the visually opaque sheath positioned in covering relation to the partially transparent sheath for reciprocating sliding movement along the length thereof;
    wherein the visually opaque sheath is of a predetermined length that relates to the plurality of distance markings displayed on the light diffusing optical fiber in that alignment of the proximal end of the visually opaque sheath with any of the plurality of distance markings corresponds with the distal end of the visually opaque sheath being spaced from the distal end of the light diffusing optical fiber by a known distance, thereby permitting determination of the length of an uncovered portion of the light diffusing fiber.

16. The device according to claim 11, wherein the partially transparent sheath is radio opaque.

17. The device according to claim 11, further comprising an in situ stabilization mechanism coupled to the partially transparent sheath.

18. The device according to claim 11, wherein the elongated light diffusing optical fiber is illuminated and the opaque sheath comprises an interior surface that is composed of a material which reflects a majority of the illuminating light.

* * * * *